(12) United States Patent
Stoer et al.

(10) Patent No.: US 10,294,238 B2
(45) Date of Patent: May 21, 2019

(54) ISOSORBIDE DIESTER AS PEARLIZING AGENT AND OPACIFIER

(71) Applicant: BASF SE, Ludwigshafen am Rhein (DE)

(72) Inventors: Claudia Stoer, Duesseldorf (DE); Markus Weissenegger, Duesseldorf (DE); Claus Nieendick, Krefeld (DE); Mirella Winzek, Titz (DE)

(73) Assignee: BASF SE, Ludwigshafen (DE)

( * ) Notice: Subject to any disclaimer, the term of this patent is extended or adjusted under 35 U.S.C. 154(b) by 15 days.

(21) Appl. No.: 15/568,503

(22) PCT Filed: Apr. 14, 2016

(86) PCT No.: PCT/EP2016/058217
§ 371 (c)(1),
(2) Date: Oct. 23, 2017

(87) PCT Pub. No.: WO2016/169833
PCT Pub. Date: Oct. 27, 2016

(65) Prior Publication Data
US 2018/0155357 A1 Jun. 7, 2018

(30) Foreign Application Priority Data
Apr. 24, 2015 (EP) ................................. 15165053

(51) Int. Cl.
C07D 493/04 (2006.01)
A61K 8/36 (2006.01)
A61K 8/37 (2006.01)
A61Q 90/00 (2009.01)
C11C 3/00 (2006.01)
C11D 3/00 (2006.01)
C11D 3/20 (2006.01)
C11D 11/00 (2006.01)

(52) U.S. Cl.
CPC ............ C07D 493/04 (2013.01); A61K 8/361 (2013.01); A61K 8/375 (2013.01); A61Q 90/00 (2013.01); C11C 3/003 (2013.01); C11D 3/0089 (2013.01); C11D 3/2079 (2013.01); C11D 3/2086 (2013.01); C11D 11/0017 (2013.01); C11D 11/0029 (2013.01); C11D 11/0035 (2013.01); C11D 11/0052 (2013.01); A61K 2800/436 (2013.01)

(58) Field of Classification Search
CPC .. A61K 8/362; C07D 495/04; C11D 11/0017; C11D 3/2079
See application file for complete search history.

(56) References Cited

U.S. PATENT DOCUMENTS

| 9,730,450 B2 * | 8/2017 | Pilz | .................. A01N 43/90 |
| 2003/0114635 A1 * | 6/2003 | Van Es | ............... C07D 493/04 528/274 |
| 2011/0117036 A1 * | 5/2011 | Chaudhuri | ........... A61K 8/4973 424/60 |
| 2012/0035090 A1 * | 2/2012 | Breffa | ................. C11D 1/662 510/220 |
| 2014/0322151 A1 | 10/2014 | Fricke et al. | |

FOREIGN PATENT DOCUMENTS

| DE | WO2013/017257 | * | 2/2013 |
| EP | 2 239 315 A1 | | 10/2010 |
| WO | WO-01/83488 A1 | | 11/2001 |
| WO | WO-2013/041388 A1 | | 3/2013 |
| WO | WO-2016/005239 A1 | | 1/2016 |

OTHER PUBLICATIONS

International Search Report for Patent Application No. PCT/EP2016/058217, dated Jun. 2, 2016.
Extended European Search Report for EP Patent Application No. 15165053.8, dated Jul. 28, 2017 (7 pages).

* cited by examiner

Primary Examiner — Johann R Richter
Assistant Examiner — Danielle Sullivan
(74) Attorney, Agent, or Firm — Marshall, Gerstein & Borun LLP

(57) ABSTRACT

A description is given of a composition comprising at least one isosorbide diester, at least one isosorbide monoester and at least one fatty acid, and also of a process for the preparation thereof. In addition, the present invention relates to the use of this composition as pearlizing agent and opacifier in cosmetic compositions and detergents.

11 Claims, No Drawings

ISOSORBIDE DIESTER AS PEARLIZING AGENT AND OPACIFIER

CROSS-REFERENCE TO RELATED APPLICATIONS

This application is the U.S. National Phase of PCT/EP2016/058217, filed Apr. 14, 2016, which claims the benefit of European Patent Application No. 15165053.8, filed Apr. 24, 2015.

The present invention relates to compositions comprising at least one isosorbide diester, at least one isosorbide monoester and at least one fatty acid, and also to processes for the preparation thereof. Another subject matter of the present invention is the use of the corresponding compositions as pearlizing agent or opacifier in cosmetic competitions and detergents.

Pearlizing agents and opacifiers are frequently used in cosmetic compositions and detergents, in order to improve the aesthetics of the corresponding preparations and to give them an especially caring appearance. In order to meet the high market demands with regard to sensory properties, new pearlizing agents and opacifiers are accordingly continually being developed and the suitability thereof in cosmetic compositions and detergents tested.

The pearlizing agents and opacifiers commercially available or described at present are still not satisfactory for use in cosmetic compositions and detergents and there accordingly furthermore exists a requirement for the provision of new ingredients which are suitable for use in cosmetic compositions or detergents as pearlizing agent or opacifier.

Special compositions comprising isosorbide derivatives have now been developed according to the invention which can advantageously be used in cosmetic compositions or detergents.

The present invention accordingly relates to a composition comprising at least one isosorbide diester as constituent (A), at least one isosorbide monoester as constituent (B) and at least one fatty acid as constituent (C).

It has been discovered, according to the invention, that a composition comprising at least one isosorbide diester, at least one isosorbide monoester and at least one fatty acid causes an improved pearlizing effect and an improved opacity effect in cosmetic compositions and detergents.

Composition

Isosorbide (or 1,4:3,6-dianhydrosorbitol) is the anhydride of sorbitol and is commercially available. It can, for example, be obtained by heating sorbitol in the presence of concentrated sulfuric or hydrochloric acid. In addition, isosorbide can be obtained starting from suitable polysaccharides after hydrolysis to give D-glucose and subsequent reduction to give D-sorbitol through intramolecular double dehydration. On an industrial scale, starch or cellulose is used as source of raw material. Isosorbide is accordingly an attractive building block for applications in the cosmetic field and in the detergent field since it is prepared from renewable raw materials.

Different isosorbide mono- and/or diesters can be obtained by processes known per se to a person skilled in the art.

The isosorbide diesters of the constituent (A) to be used according to the invention exhibit the general formula (I):

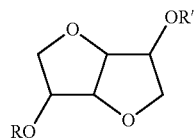

(I)

in which R and R' are each time, independently of one another, a COR" radical in which R" is a linear or branched and saturated or unsaturated alkyl radical with 5 to 23 carbon atoms. The isosorbide diester to be used according to the invention can accordingly be a homogeneous or mixed diester.

The isosorbide monoesters of the constituent (B) to be used according to the invention exhibit the general formula (II):

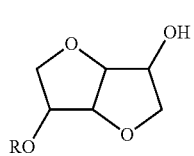

(II)

in which R is a COR' radical in which R' is a linear or branched and saturated or unsaturated alkyl radical with 5 to 23 carbon atoms.

The general formulae (I) and (II) represented above also comprise, in the context of the present invention, all stereoisomers of the isosorbide, in particular isoidide and isomannide, and also any mixtures thereof. Furthermore, the general formula (I) also comprises all combinations of the R and R' radicals with one another.

Constituent (A)—Isosorbide Diester

An isosorbide diester is used as constituent (A) in the composition according to the invention. It preferably concerns here a diester of isosorbide with a $C_6$ to $C_{24}$ fatty acid of the general formula (I), which has already been described above.

The saturated $C_6$ to $C_{24}$ fatty acids are possible in particular as fatty acids for the formation of the isosorbide diester. These are preferably chosen from the group consisting of hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, heneicosanoic acid, behenic acid and lignoceric acid.

The monounsaturated $C_6$ to $C_{24}$ fatty acids are also possible in particular as fatty acids for the formation of the isosorbide diester. These are preferably chosen from the group consisting of undecylenic acid, myristoleic acid, palmitoleic acid, petroselenic acid, oleic acid, elaidic acid, vaccenic acid, gadoleic acid, eicosenoic acid, cetoleic acid, erucic acid and nervonic acid.

The polyunsaturated $C_6$ to $C_{24}$ fatty acids are also possible in particular as fatty acids for the formation of the isosorbide diester. These are preferably chosen from the group consisting of linoleic acid, α-linolenic acid, γ-linolenic acid, calendic acid, punicic acid, α-eleostearic acid, β-eleostearic acid, arachidonic acid, timnodonic acid, clupanodonic acid and cervonic acid.

In a preferred embodiment, the isosorbide diester is a diester of isosorbide with a $C_{10}$ to $C_{22}$ fatty acid, more preferably a diester of isosorbide with a $C_{12}$ to $C_{20}$ fatty acid and more preferably still a diester of isosorbide with a $C_{16}$ to $C_{18}$ fatty acid.

In the context of the present invention, the diesters of isosorbide with a $C_{16}$ to $C_{18}$ fatty acid have in particular proven to be suitable for achieving the desired pearlizing properties and opacifier properties in cosmetic compositions and detergents.

Accordingly, in an additional even more preferred embodiment of the composition according to the invention, the constituent (A) is an isosorbide diester chosen from the group consisting of isosorbide distearate, isosorbide dipalmitate, isosorbide palmitate stearate and mixtures of the abovementioned compounds.

Furthermore, the constituent (A) of the composition according to the invention is in particular a mixture of diesters of the isosorbide, a mixture of isosorbide diesters comprising isosorbide distearate being particularly preferred.

In a very particularly preferred embodiment of the composition according to the invention, the constituent (A) is a mixture of isosorbide distearate, isosorbide dipalmitate and isosorbide palmitate stearate.

If, in the context of the present invention, this particularly preferred mixture of isosorbide distearate and isosorbide dipalmitate is used as constituent (A), the weight ratio of isosorbide dipalmitate to isosorbide distearate in the composition is preferably 45:55 to 1:99, more preferably 40:60 to 1:99, more preferably still 30:70 to 1:99, more preferably still 30:70 to 2:98. When use is made of a mixture of isosorbide distearate and isosorbide dipalmitate with the relative proportions mentioned above, i.e. in particular with an excess of isosorbide distearate, the pearlizing properties and the opacifier properties are very particularly pronounced.

The constituent (A) can, in the composition according to the invention, be comprised in an amount of at least 70% by weight, based on the composition.

The constituent (A) is preferably comprised in the composition according to the invention in an amount of 75% by weight to 95% by weight, more preferably 80% by weight to 90% by weight and more preferably still 82% by weight to 88% by weight, each time based on the composition, in order to obtain a good pearlizing effect and opacifier effect.

Constituent (B)—Isosorbide Monoester

An isosorbide monoester is used as constituent (B) in the composition according to the invention. It preferably concerns here a monoester of isosorbide with a $C_6$ to $C_{24}$ fatty acid of the general formula (II), which has already been described above.

The same fatty acids which are also used above for the constituent (A), the isosorbide diester, are possible for the preparation of the isosorbide monoester. In this respect, reference is made to the above embodiments.

In a preferred embodiment, the composition according to the invention comprises an isosorbide monoester with a $C_{16}$ to $C_{18}$ fatty acid which likewise is preferred for achieving the desired pearlizing properties and opacifier properties in cosmetic compositions and detergents.

Accordingly, in a preferred embodiment of the composition according to the invention, the constituent (B) is an isosorbide monoester chosen from the group consisting of isosorbide monostearate, isosorbide monopalmitate and mixtures of the abovementioned compounds.

Furthermore, the constituent (B) of the composition according to the invention is in particular a mixture of monoesters of the isosorbide, a mixture of isosorbide monoesters comprising isosorbide monostearate being particularly preferred.

In a very particularly preferred embodiment, the constituent (B) is a mixture of isosorbide monostearate and isosorbide monopalmitate.

If, in the context of the present invention, this particularly preferred mixture of isosorbide monostearate and isosorbide monopalmitate is used as constituent (B), the weight ratio of isosorbide monopalmitate to isosorbide monostearate in the composition is preferably 45:55 to 1:99, more preferably 40:60 to 1:99, more preferably still 30:70 to 1:99, more preferably still 30:70 to 2:98. When use is made of a mixture of isosorbide monostearate and isosorbide monopalmitate in the relative proportions mentioned above, the pearlizing properties and the opacifier properties are very particularly pronounced.

The constituent (B) can, in the composition according to the invention, be comprised in an amount of at least 0.01% by weight, based on the composition.

The constituent (B) is preferably comprised in the composition according to the invention in an amount of 0.01% by weight to 20% by weight, more preferably 0.5% by weight to % by weight and more preferably still 1% by weight to 10% by weight, each time based on the composition, in order to obtain a good pearlizing effect and opacifier effect.

Constituent (C)—Fatty Acid

A fatty acid is used as constituent (C) in the composition according to the invention. It preferably concerns here a fatty acid which has already been used above for the preparation of the isosorbide diester or isosorbide monoester. In this respect, reference is made to the above embodiments.

In a preferred embodiment, the composition according to the invention comprises a $C_{16}$ to $C_{18}$ fatty acid which is particularly preferably chosen from the group consisting of stearic acid, palmitic acid and mixtures thereof.

In a very particularly preferred embodiment, the constituent (B) is a mixture of stearic acid and palmitic acid.

If, in the context of the present invention, a mixture of stearic acid and palmitic acid is used as constituent (C), the weight ratio of palmitic acid to stearic acid in the composition is thus preferably 45:55 to 1:99, more preferably 40:60 to 1:99, more preferably still 30:70 to 1:99, more preferably still 30:70 to 2:98.

The constituent (C) can, in the composition according to the invention, be comprised in an amount of at least 1% by weight, based on the composition.

The constituent (C) is preferably comprised in the composition according to the invention in an amount of 1% by weight to 30% by weight, more preferably 3% by weight to 25% by weight and more preferably still 5% by weight to 20% by weight, each time based on the composition.

PREFERRED EMBODIMENTS OF THE COMPOSITION ACCORDING TO THE INVENTION

Particularly preferred embodiments of the composition according to the invention are described below.

In a first particularly preferred embodiment, the composition according to the invention comprises:
  at least one isosorbide diester as constituent (A) in an amount of 75% by weight to 95% by weight,
  at least one isosorbide monoester as constituent (B) in an amount of 0.01% by weight to 20% by weight, and at least one fatty acid as constituent (C) in an amount of 1% by weight to 30% by weight, the figures for amounts being each time based on the composition.

In a second particularly preferred embodiment, the composition according to the invention comprises:
at least one isosorbide diester as constituent (A) in an amount of 80% by weight to 90% by weight,
at least one isosorbide monoester as constituent (B) in an amount of 0.5% by weight to 15% by weight, and
at least one fatty acid as constituent (C) in an amount of 3% by weight to 25% by weight, the figures for amounts being each time based on the composition.

In a third preferred embodiment, the composition according to the invention comprises:
at least one isosorbide diester as constituent (A) in an amount of 82% by weight to 88% by weight,
at least one isosorbide monoester as constituent (B) in an amount of 1% by weight to 10% by weight, and
at least one fatty acid as constituent (C) in an amount of 5% by weight to 20% by weight, the figures for amounts being each time based on the composition.

In the first to third embodiments described above, the compositions according to the invention are in particular characterized in that the isosorbide diester is a mixture of isosorbide distearate, isosorbide dipalmitate and isosorbide palmitate stearate, the isosorbide monoester is a mixture of isosorbide monostearate and isosorbide monopalmitate and the fatty acid is a mixture of stearic acid and palmitic acid.

In the first to third embodiments described above, the compositions according to the invention in addition are in particular characterized by:
the ratio of isosorbide dipalmitate to isosorbide distearate in the composition being 45:55 to 1:99, more preferably 40:60 to 1:99, more preferably still 30:70 to 1:99, more preferably still 30:70 to 2:98;
the ratio of isosorbide monopalmitate to isosorbide monostearate in the composition being 45:55 to 1:99, more preferably 40:60 to 1:99, more preferably still 30:70 to 1:99, more preferably still 30:70 to 2:98; and
the ratio of palmitic acid to stearic acid in the composition being 45:55 to 1:99, more preferably 40:60 to 1:99, more preferably still 30:70 to 1:99, more preferably still 30:70 to 2:98.

In a very particularly preferred embodiment of the present invention, the composition according to the invention comprises:
isosorbide distearate, isosorbide dipalmitate and isosorbide palmitate stearate in an amount of 82 to 88% by weight, based on the composition, with a ratio of isosorbide dipalmitate to isosorbide distearate of 30:70 to 2:98;
isosorbide monostearate and isosorbide monopalmitate in an amount of 1 to 10% by weight, based on the composition, with a ratio of isosorbide monopalmitate to isosorbide monostearate of 30:70 to 2:98; and
stearic acid and palmitic acid in an amount of 5 to 20% by weight, based on the composition, with a ratio of palmitic acid to stearic acid of 30:70 to 2:98.

In an additional preferred independent embodiment of the present invention, the composition according to the invention is characterized in that the weight ratio of diesters of the isosorbide to monoesters of the isosorbide is at least 4:1, more preferably at least 6:1, more preferably still at least 8:1, more preferably still at least 10:1.

In an additional independent embodiment of the present invention, the composition according to the invention is characterized in that the amount of isosorbide distearate, isosorbide monostearate and stearic acid is at least 70% by weight, more preferably at least 80% by weight and more preferably still at least 90% by weight.

The isosorbide esters used in the composition according to the invention can be synthesized by esterification processes known per se. WO 01/83488 A discloses, by way of example, a suitable method by which mono-or diesters of the isosorbide or mixtures of mono- and diesters of the isosorbide can be obtained.

The present invention accordingly also relates to a process for the preparation of a composition according to the invention which is characterized by an esterification product being obtained by the process stage of the esterification of isosorbide with at least one fatty acid.

The process according to the invention can in this connection be carried out in the presence of an esterification catalyst, zinc oxalate representing a suitable catalyst.

If, in the context of the present invention, an esterification catalyst is used, the esterification catalyst used is generally deactivated after the esterification reaction; in particular, the esterification catalyst used is hydrolyzed.

Subsequent to the esterification reaction and the deactivation of the catalyst which is optionally to be carried out, the resulting reaction product is usually purified, for example by filtration or distillation under vacuum.

The esterification itself is generally carried out at a temperature of 160 to 230° C., more preferably 170 to 220° C. and more preferably still 180 to 220° C.

It should be taken into consideration, in the preparation of the mono- and diesters of the isosorbide, that, depending on the excess of the isosorbide used or of the fatty acid, a variable ratio of mono- and diester is produced since the two hydroxyl groups, due to their exo- or endo-arrangement, have different reactivities.

In the process according to the invention, an excess of fatty acid to isosorbide of at least 2.05 equivalents of fatty acid, based on 1 equivalent of isosorbide, is generally used. Particular preference is given to an excess of fatty acid to isosorbide of 2.05 to 2.5 equivalents, more preferably 2.1 to 2.4 equivalents and more preferably still 2.2 to 2.3 equivalents, each time based on 1 equivalent of isosorbide.

The process according to the invention is generally carried out, with this excess of fatty acid, for long enough for the amounts of constituents (A), (B) and (C) defined according to the invention in the claimed composition to be obtained. This is ascertainable by a person skilled in the art with the usual measures, for example by means of GC monitoring and acid number determination. Accordingly, the composition according to the invention is preferably prepared in a one-pot reaction, in which the isosorbide diesters and isosorbide monoesters are formed simultaneously starting from isosorbide and one or more fatty acids. Through the use of an excess of fatty acid, a residue of this likewise remains in the composition according to the invention. Admittedly, the composition according to the invention can also be prepared through the mixing of the individual constituents.

Use in Cosmetic Compositions

The composition according to the invention can preferably be used as pearlizing agent in cosmetic compositions, in particular surface-active cosmetic compositions. The cosmetic compositions, in particular surface-active cosmetic compositions, are generally liquid cosmetic compositions.

"Cosmetic compositions" are to be understood here as all compositions known to a person skilled in the art which are exclusively or primarily intended to be applied externally to the human body or oral cavity for the cleaning, caring, protection, maintaining a good condition, perfuming, changing the appearance or for influencing body odor.

The cosmetic compositions according to the invention can in particular be formulations for body care, for example a body milk, creams, lotions, sprayable emulsions, products for eliminating body odor, and the like. The hydrocarbons can also be used in surfactant-containing formulations, such as, for example, foam baths, shower gels, shampoos and care rinses. According to the end application, the cosmetic formulations comprise a series of further auxiliaries and additives, such as, for example, surfactants, further oil bodies, emulsifiers, pearlizing waxes, bodying agents, thickeners, superfatting agents, stabilizers, polymers, fats, waxes, lecithins, phospholipids, biogenic active ingredients, UV sunscreen factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, and the like, which are listed below by way of example.

Anionic, nonionic, cationic and/or amphoteric or zwitterionic surfactants may be comprised as surface-active substances (surfactants). At least one anionic surfactant is preferably comprised in surfactant-containing cosmetic formulations, such as, for example, shower gels, foam baths, shampoos, and the like. The proportion of the surfactants here is generally about 1 to 30%, preferably 5 to 25% and especially 10 to 20% by weight.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates. If the anionic surfactants comprise polyglycol ether chains, these may exhibit a conventional homolog distribution but preferably a narrow homolog distribution. Typical examples of nonionic surfactants are fatty alcohol polyglycol ethers, alkylphenol polyglycol ethers, fatty acid polyglycol esters, fatty acid amide polyglycol ether, fatty amine polyglycol ethers, alkoxylated triglycerides, mixed ethers or mixed formals, optionally partially oxidized glucuronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants comprise polyglycol ether chains, these may exhibit a conventional homolog distribution but preferably a narrow homolog distribution. Typical examples of cationic surfactants are quarternary ammonium compounds, such as, for example, dimethyldistearylammonium chloride, and esterquats, in particular quaternized fatty acid trialkanolamine ester salts. Typical examples of amphoteric or zwitterionic surfactants are alkyl betaines, alkyl amido betaines, aminopropionates, aminoglycinates, imidazolinium betaines and sulfobetaines. The surfactants mentioned are exclusively known compounds. With regard to the structure and preparation of these substances, reference may be made to relevant review works in this field. Typical examples of particularly suitable mild, i.e. particularly skin-friendly, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, fatty acid glucamides, alkyl amido betaines, amphoacetals and/or protein fatty acid condensates, the latter preferably based on soya or wheat proteins.

Body care compositions, such as creams, lotions and milks, typically comprise a number of further oil bodies and emollients, which contribute to further optimization of the sensory properties. The oil bodies are generally comprised in a total amount of 1 to 50% by weight, preferably 5 to 25% by weight and in particular 5 to 15% by weight. As further oil bodies come, for example, Guerbet alcohols based on fatty alcohols having 6 to 18, preferably 8 to 10, carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Additionally suitable are esters of linear $C_6$-$C_{22}$ fatty acids with branched alcohols, in particular 2-ethylhexanol, esters of $C_{18}$-$C_{38}$ alkylhydroxycarboxylic acids with linear or branched $C_6$-$C_{22}$ fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$ alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols.

Fats and waxes are added to the body care products as care substances, and also in order to increase the consistency of the cosmetics. Typical examples of fats are glycerides, i.e. solid vegetable or animal products which are composed essentially of mixed glyceryl esters of higher fatty acids. Fatty acid partial glycerides, i.e. technical-grade mono- and/or diesters of glycerol with fatty acids having 12 to 18 carbon atoms, such as, for instance, glyceryl mono/dilaurate, -palmitate or -stearate, are also possible for this purpose. Possible waxes are, inter alia, natural waxes, such as, for example, candelilla wax, carnauba wax, japan wax, esparto grass wax, cork wax, guaruma wax, rice bran wax, sugarcane wax, ouricury wax, montan wax, beeswax, shellac wax, spermaceti, lanolin (wool wax), uropygial grease, ceresin, ozokerite (earth wax), petrolatum, paraffin waxes, micro waxes; chemically modified waxes (hard waxes), such as, for example, montan ester waxes, Sasol waxes, hydrogenated jojoba waxes, and also synthetic waxes, such as, for example, polyalkylene waxes and polyethylene glycol waxes. As well as the fats, fat-like substances, such as lecithins and phospholipids, are also possible as additives. Examples of natural lecithins which may be mentioned are the cephalins, which are also referred to as phosphatidic acids and are derivatives of 1,2-diacyl-sn-glycero-3-phosphoric acids. In contrast, phospholipids are usually understood to mean mono- and preferably diesters of phosphoric acid with glycerol (glyceryl phosphates), which are generally counted among the fats. In addition, sphingosines or sphingolipids are also possible.

Suitable thickeners are, for example, Aerosil grades (hydrophilic silicas), polysaccharides, in particular xanthan gum, guar, agar, alginates and tyloses, carboxymethylcellulose, hydroxyethylcellulose and hydroxypropylcellulose, polyvinyl alcohol, polyvinylpyrrolidone and bentonites, such as, for example, Bentone® Gel VS-5PC (Rheox).

UV light protection factors are understood to mean, for example, organic substances (light protection screening agents) which are liquid or crystalline at room temperature and which are capable of absorbing ultraviolet rays and of again releasing the energy absorbed in the form of radiation of longer wavelength, for example heat. UV-B screening agents can be oil-soluble or water-soluble. Benzoylmethane derivatives are possible in particular as typical UV-A screening agents. The UV-A and UV-B screening agents can, of course, also be used in mixtures, e.g. combinations of the benzoylmethane derivatives, e.g. 4-tertbutyl-4'-methoxydibenzoylmethane (Parsol® 1789), and 2-ethylhexyl 2-cyano-3,3-diphenylcinnamate (octocrylene), and also esters of cinnamic acid, preferably 2-ethylhexyl 4-methoxycinnamate and/or propyl 4-methoxycinnamate and/or isoamyl 4-methoxycinnamate. Such combinations are frequently, combined with water-soluble screening agents, such as, for example, 2-phenylbenzimidazole-5-sulfonic acid and the alkali metal, alkaline earth metal, ammonium, alkylammonium, alkanolammonium and glucammonium salts thereof.

Apart from the soluble substances mentioned, insoluble light protection pigments, namely finely dispersed metal oxides, are also possible. Examples of suitable metal oxides are in particular zinc oxide and titanium dioxide. Apart from the two abovementioned groups of primary light protection substances, it is also possible to use secondary light protection agents of the antioxidant type, which interrupt the photochemical reaction chain which is triggered when UV radiation penetrates into the skin.

Biogenic active ingredients are understood to mean, for example, tocopherol, tocopherol acetate, tocopherol palmitate, ascorbic acid, (deoxy)ribonucleic acid and the fragmentation products thereof, β-glucans, retinol, bisabolol, allantoin, phytantriol, panthenol, AHA acids, amino acids, ceramides, pseudoceramides, essential oils, plant extracts, such as, for example, *Prunus* extract, bambara nut extract and vitamin complexes.

Deodorizing active ingredients counteract body odors, conceal or remove them. Body odors arise through the action of skin bacteria on apocrine perspiration, which forms unpleasant-smelling degradation products. Correspondingly suitable as deodorizing active ingredients are, inter alia, germination inhibitors, enzyme inhibitors, odor absorbers or odor masking agents.

Possible insect repellents are, for example, N,N-diethyl-m-toluamide, 1,2-pentanediol or ethyl 3-(N-(n-butyl)-N-acetylamino)propionate, which is sold under the description Insect Repellent® 3535 by Merck KGaA, and also butyl acetylaminopropionates.

Dihydroxyacetone is suitable as self-tanning agent. Possible tyrosine inhibitors, which prevent the formation of melanin and are applied in depigmenting compositions, are, for example, arbutin, ferulic acid, kojic acid, coumaric acid and ascorbic acid (vitamin C).

Examples of suitable preservatives are phenoxyethanol, formaldehyde solution, parabens, pentanediol or sorbic acid, and also the silver complexes known under the description Surfacine®, and the additional substance classes listed in Annex 6, parts A and B, of the Cosmetics Directive.

Mention may be made, as perfume oils, of mixtures of natural and synthetic odorants. Natural odorants are extracts of flowers, stems and leaves, fruit, fruit shells, roots, wood, herbs and grasses, needles and branches, resins and balsams. Additionally possible are animal raw materials, such as, for example, civet and castoreum, and also synthetic odorant compounds of the ester, ether, aldehyde, ketone, alcohol and hydrocarbon type.

The cosmetic compositions comprise the compositions claimed according to the invention as pearlizing agent. Admittedly, the cosmetic compositions can also comprise additional pearlizing agents. In this sense, the following, for example, are possible as pearlizing waxes, in particular for use in surface-active formulations: alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted, carboxylic acids with fatty alcohols having 6 to 22 carbon atoms, especially long-chain esters of tartaric acid; fatty substances, such as, for example, fatty alcohols, fatty ketones, fatty aldehydes, fatty ethers and fatty carbonates, which have in total at least 24 carbon atoms, especially laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols (without the sorbitan derivatives) having 2 to 15 carbon atoms and 2 to 10 hydroxyl groups, and mixtures thereof.

Use may be made, as superfatting agents, of substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers.

Use may be made, as stabilizers, of metal salts of fatty acids, such as, e.g., magnesium stearate or ricinoleate, aluminum stearate or ricinoleate and/or zinc stearate or ricinoleate.

Use may furthermore be made, in order to improve the flow behavior, of hydrotropes, such as, for example, ethanol, isopropyl alcohol or polyols. Polyols which are suitable here preferably have 2 to 15 carbon atoms and at least two hydroxyl groups. The polyols may comprise still other functional groups, in particular amino groups, or be modified with nitrogen.

In particular, those cosmetic compositions are preferred which exhibit an aqueous phase and an oily phase simultaneously and exist, e.g., in the form of an emulsion (both water-in-oil and oil-in-water) and which comprise, as a constituent, one or more isosorbide derivatives according to the above definition. In this connection, the isosorbide derivatives can be used as oily phase or emollient, or as constituent of the oily phase. However, as is still explained subsequently, they can, depending on their structure, also impart certain functional properties.

The composition according to the invention is used in the cosmetic compositions as pearlizing agent, preferably in an amount of at least 0.1% by weight, based on the cosmetic composition.

The composition according to the invention is preferably used in the cosmetic composition in an amount of 0.1 to 12% by weight, more preferably 0.5 to 6% by weight and more preferably still 0.75 to 3.5% by weight, each time based on the cosmetic composition, in particular surface-active cosmetic composition.

Use in Detergents

The composition according to the invention can in addition preferably be used as opacifier in detergents, in particular surface-active detergents. The detergents, in particular surface-active detergents, are generally liquid detergents.

Appropriate detergents comprise anionic and/or amphoteric and/or nonionic surfactants, and also water and optionally additional ingredients typical for such compositions.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates. If the anionic surfactants comprise polyglycol ether chains, these may exhibit a conventional homolog distribution but preferably a narrow homolog distribution.

Typical examples of nonionic surfactants are fatty alcohol polyglycol ethers, alkylphenol polyglycol ethers, fatty acid polyglycol esters, fatty acid amide polyglycol ether, fatty amine polyglycol ethers, alkoxylated triglycerides, mixed ethers or mixed formals, optionally partially oxidized glucuronic acid derivatives, fatty acid N-alkylglucamides, protein hydrolysates (in particular wheat-based vegetable products), polyol fatty acid esters, sugar esters, sorbitan esters, polysorbates and amine oxides.

If the nonionic surfactants comprise polyglycol ether chains, these may exhibit a conventional homolog distribution but preferably a narrow homolog distribution. Typical examples of cationic surfactants are quaternary ammonium compounds and esterquats, in particular quaternized fatty acid trialkanolamine ester salts.

Typical examples of amphoteric or zwitterionic surfactants are alkyl betaines, alkyl amido betaines, aminopropionates, aminoglycinates, imidazolinium betaines and sulfobetaines. Anionic surfactants are particularly preferably comprised and here in particular alkyl ether sulfates.

Alkyl ether sulfates ("ether sulfates") represent known anionic surfactants which are prepared on an industrial scale by $SO_3$— or chlorosulfonic acid (CSA) sulfation of fatty alcohol or oxo alcohol polyglycol ethers and subsequent neutralization. Within the meaning of the invention, suitable ether sulfates are those which follow the formula (II), $R^2O(CH_2CH_2O)_mSO_3X$ (II), in which $R^2$ is a linear or branched alkyl and/or alkenyl radical having 6 to 22 carbon atoms, n is a number from 1 to 10 and X is an alkali metal and/or alkaline earth metal, ammonium, alkylammonium, alkanolammonium or glucammonium. Typical examples are the sulfates of addition products of an average of 1 to 10 and particularly 2 to 5 mol of ethylene oxide to caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, arachidyl alcohol, gadoleyl alcohol, behenyl alcohol, erucyl alcohol and brassidyl alcohol and also technical-grade mixtures thereof in the form of their sodium and/or magnesium salts. The ether sulfates may in this connection exhibit both a conventional and a narrowed homolog distribution. Particular preference is given to the use of ether sulfates based on adducts of an average of 2 to 3 mol of ethylene oxide to technical-grade $C_{12/14}$ or $C_{12/18}$ coconut fatty alcohol fractions in the form of their sodium and/or magnesium salts.

The cleaning agents can furthermore comprise dyes, fragrances, pearlizing agents, opacifiers, complexing agents, inorganic or organic acids and/or bases, builders, bleaches, antifoaming agents, but also polymers (e.g. as thickeners but also as builders), hydrotopes or solubility promoters and the like. Preferably, the cleaning agent comprises polymers, reference being made to the details of the above description for this. These substances are then used generally in amounts of altogether up to 20% by weight, preferably, however, only up to a maximum of 15% by weight, in particular of 1.5 to 5% by weight, each time based on the total weight of the cleaning agent.

The pH of the cleaning agent is preferably in the range from 5.0 to 10.0, preferably 5.5 to 8.0. The cleaning agent preferably exhibits a pH in the range from 6 to 7.5. However, with acidic cleaning agents, which are frequently used in the bath sector, lower pHs, typically from 2 to 5, preferably from 3.5 to 4.5, are clearly also possible.

The detergents described in the context of the present invention can in particular be used for the cleaning of woven goods, knitwear and/or fulled goods, in particular textiles, carpets and/or curtains. In addition, the detergents are suitable for the cleaning of necessary articles. In the context of the present invention, the term "necessary articles" is understood to mean articles which are to be subsumed to the regulation of § 2 Section 6 LFGB [German Food and Feed Code].

In addition, the detergents according to the invention are suitable for the cleaning of hard surfaces, in particular of metal, glass, porcelain, ceramic, tiles, stone, varnished surfaces, plastics, wood and/or leather, and can be used in mechanical cleaning.

The composition according to the invention is used in the detergent as opacifier, preferably in an amount of at least 0.1% by weight, based on the detergent.

The composition according to the invention is preferably used in the detergent in an amount of 0.1 to 12% by weight, more preferably 0.5 to 6% by weight and more preferably still 1 to 3.5% by weight, each time based on the detergent, in particular surface-active detergent.

EXEMPLARY EMBODIMENTS

The investigations described below were carried out on the properties of the isosorbide derivatives. Insofar as ingredients are mentioned, the INCI nomenclature has been used.

The test substances were incorporated in a cosmetic formulation.

The pearlizing was assessed optically by comparison with a standard, the pearlizing wax (EGDS=Cutina AGS), and rated on a scale from 0 to 2 (0=poorer pearlizing than the standard, 1=pearlizing comparable with the standard, 2=better pearlizing than the standard).

|  | $C_{16}$ and $C_{18}$ carbon chain distribution | | GC wt % | | |
| --- | --- | --- | --- | --- | --- |
|  | % $C_{16}$ | % $C_{18}$ | Monoester | Diester | Fatty acid |
| Sample 1 | 2 | 98 | 6 | 86 | 8 |
| Sample 2 | 30 | 70 | 3 | 89 | 8 |
| Sample 3 | 45 | 55 | 4 | 83 | 13 |
| Sample 4 | 30 | 70 | 33 | 65 | 2 |

Formulation 1

|  | % by weight |
| --- | --- |
| Test substance Sample 1-4 | 20 |
| Comperlan ® 100 | 2 |
| (INCI: Cocamide MEA) |  |
| Texapon ® N 70 | 22 |
| (Coconut fatty alcohol + 2EO-sulfate, sodium salt; 79%) |  |
| Sodium benzoate | 0.5 |
| Sodium chloride | 1.0 |
| Citric acid (50%) | 0.5 |
| Water | To 100 | pH: 4-5 pH: 4-5

The pearlizing effect (brilliancy) was determined as 5% by weight aqueous diluting of formulation 1.

|  | Pearlizing effect of formulation 1 with |
| --- | --- |
| Sample 1 | 1 |
| Sample 2 | 2 |
| Sample 3 | 1-2 |
| Sample 4 | 0 |

Formulation 1 with samples 1 to 4 all show a pearlizing. Formulation 1 with sample 1 to sample 3 shows a better pearlizing than or an equivalent pearlizing to a formulation with an equivalent amount of standard pearlizing agent (EGDS=Cutina AGS). Formulation 1 with sample shows absolutely the best pearlizing, which is also clearly better than the standard.

The invention claimed is:

1. A composition comprising
at least 70% by weight of a mixture of isosorbide distearate, isosorbide dipalmitate, and isosorbide palmitate stearate as constituent (A),
0.01% by weight to 20% by weight of a mixture of isosorbide monostearate and isosorbide monoplamitate as constituent (B) and
1 to 30% by weight of a mixture of stearic acid and palmitic acid as constituent (C).

2. The composition according to claim 1, wherein the weight ratio of isosorbide dipalmitate to isosorbide distearate in the composition is 45:55 to 1:99, the weight ratio of isosorbide monopalmitate to isosorbide monostearate in the composition is 45:55 to 1:99, and the weight ratio of palmitic acid to stearic acid in the composition is 45:55 to 1:99.

3. The composition according to claim 1 comprising:
isosorbide distearate, isosorbide dipalmitate, and isosorbide palmitate stearate in an amount of 82 to 88% by weight, based on the composition, with a ratio of isosorbide dipalmitate to isosorbide distearate of 30:70 to 2:98;
isosorbide monostearate and isosorbide monopalmitate in an amount of 1 to 10% by weight, based on the composition, with a ratio of isosorbide monopalmitate to isosorbide monostearate of 30:70 to 2:98; and
stearic acid and palmitic acid in an amount of 5 to 20% by weight, based on the composition, with a ratio of palmitic acid to stearic acid of 30:70 to 2:98.

4. The composition according to claim 1, wherein a weight ratio of diesters of the isosorbide to monoesters of the isosorbide is at least 4:1.

5. The composition according to claim 1, wherein an amount of isosorbide distearate, isosorbide monostearate and stearic acid is at least 70% by weight, based on the composition.

6. A process for the preparation of a composition according to claim 1, wherein an esterification product is obtained by esterifying an isosorbide with at least one fatty acid.

7. The process according to claim 6, wherein, in the esterification, an excess of fatty acid to isosorbide of at least 2.05 equivalents of fatty acid, based on 1 equivalent of isosorbide is used.

8. A method of pearlizing and/or opacifying a cosmetic a cosmetic composition or a detergent comprising the use of a composition according to claim 1 as a pearlizing agent and/or opacifier.

9. The method according to claim 8 wherein the cosmetic composition or detergent is a hand cleanser or wool detergent.

10. The method according to claim 8 for the cleaning of hard surfaces selected from the group consisting of metal, glass, porcelain, ceramic, tiles, stone, varnished surfaces, plastics, wood, and leather.

11. The method according to claim 9 for cleaning woven goods, knitwear, textiles, carpets, and/or curtains.

* * * * *